(12) United States Patent
Batchelor et al.

(10) Patent No.: US 11,547,469 B2
(45) Date of Patent: *Jan. 10, 2023

(54) RECONFIGURABLE INSTRUMENT

(71) Applicant: GYRUS ACMI, INC., Southborough, MA (US)

(72) Inventors: Kester J. Batchelor, Mound, MN (US); Riyad Moe, Madison, WI (US)

(73) Assignee: Gyrus ACMI, Inc., Westborough, MA (US)

( * ) Notice: Subject to any disclaimer, the term of this patent is extended or adjusted under 35 U.S.C. 154(b) by 411 days.

This patent is subject to a terminal disclaimer.

(21) Appl. No.: 16/797,765

(22) Filed: Feb. 21, 2020

(65) Prior Publication Data
US 2020/0188013 A1     Jun. 18, 2020

Related U.S. Application Data

(63) Continuation of application No. 15/701,934, filed on Sep. 12, 2017, now Pat. No. 10,610,291.
(Continued)

(51) Int. Cl.
*A61B 18/14* (2006.01)
*A61B 18/00* (2006.01)
*A61B 18/12* (2006.01)

(52) U.S. Cl.
CPC ............ *A61B 18/1445* (2013.01); *A61B 2018/00607* (2013.01); *A61B 2018/00654* (2013.01);
(Continued)

(58) Field of Classification Search
CPC ...... A61B 18/1445; A61B 2018/00607; A61B 2018/00654; A61B 2018/00875;
(Continued)

(56) References Cited

U.S. PATENT DOCUMENTS 4,041,952 A    8/1977    Morrison, Jr. et al.
4,181,826 A    1/1980    Latasiewicz
(Continued)

FOREIGN PATENT DOCUMENTS

CN    1611192 A    5/2005
CN    101056593 A    10/2007
(Continued)

OTHER PUBLICATIONS

"U.S. Appl. No. 15/701,934, Corrected Notice of Allowability dated Mar. 11, 2020", 2 pgs.
(Continued)

*Primary Examiner* — Michael F Peffley
*Assistant Examiner* — Bo Ouyang
(74) *Attorney, Agent, or Firm* — Schwegman Lundberg & Woessner, P.A.

(57) ABSTRACT

An instrument including working arms and a moveable member. The working arms include a first arm, a second arm, a first electrode located on the first arm, and a second electrode located on the second arm. The moveable member includes a passive circuit element, a first terminal, and a second terminal. The moveable member is moveable to a first position and a second position. In the first position, the first terminal is in electrical communication with the first electrode and the second terminal is in electrical communication with the second electrode so that in the first position an electrical circuit is completed. An impedance is measured of the passive circuit element in the completed electrical circuit. The instrument is adapted to provide a modality based on the measured impedance or a determined position of the moveable member.

20 Claims, 5 Drawing Sheets

Related U.S. Application Data

(60) Provisional application No. 62/399,615, filed on Sep. 26, 2016.

(52) U.S. Cl.
CPC ............ *A61B 2018/00875* (2013.01); *A61B 2018/00916* (2013.01); *A61B 2018/00922* (2013.01); *A61B 2018/00928* (2013.01); *A61B 2018/00946* (2013.01); *A61B 2018/00958* (2013.01); *A61B 2018/126* (2013.01); *A61B 2018/1455* (2013.01); *A61B 2018/1462* (2013.01); *A61B 2018/1467* (2013.01)

(58) Field of Classification Search
CPC ........... A61B 2018/00916; A61B 2018/00922; A61B 2018/00928; A61B 2018/00946; A61B 2018/00958; A61B 2018/126; A61B 2018/1455; A61B 2018/1462; A61B 2018/1467
See application file for complete search history.

(56) References Cited

U.S. PATENT DOCUMENTS

| | | | |
|---|---|---|---|
| 4,256,931 A | 3/1981 | Palisek | |
| 4,319,099 A | 3/1982 | Asher | |
| 4,703,139 A | 10/1987 | Dunlap | |
| 4,846,516 A | 7/1989 | Yuh et al. | |
| 5,376,765 A | 12/1994 | Holmes et al. | |
| 5,399,823 A | 3/1995 | Mccusker | |
| 5,472,442 A | 12/1995 | Klicek | |
| 5,743,384 A | 4/1998 | Clark | |
| 6,016,439 A | 1/2000 | Acker | |
| 6,113,596 A | 9/2000 | Hooven et al. | |
| 6,190,386 B1 | 2/2001 | Rydell | |
| 6,310,308 B1 | 10/2001 | Watson et al. | |
| 6,423,918 B1 | 7/2002 | King et al. | |
| 6,679,882 B1 | 1/2004 | Kornerup | |
| 7,156,846 B2 * | 1/2007 | Dycus .................... | A61B 18/00 606/41 |
| 7,179,258 B2 | 2/2007 | Buysse et al. | |
| 7,232,440 B2 | 6/2007 | Dumbauld et al. | |
| 7,282,048 B2 | 10/2007 | Goble et al. | |
| 7,687,734 B2 | 3/2010 | Weber | |
| 7,902,474 B2 | 3/2011 | Mittleman et al. | |
| 8,089,017 B2 | 1/2012 | Chen et al. | |
| 8,251,989 B1 | 8/2012 | Newton et al. | |
| 8,262,655 B2 | 9/2012 | Ghabrial et al. | |
| 8,378,240 B2 | 2/2013 | Rajagopal et al. | |
| 8,568,418 B2 | 10/2013 | Matusaitis et al. | |
| 8,670,816 B2 | 3/2014 | Green et al. | |
| 8,702,702 B1 | 4/2014 | Edwards et al. | |
| 10,610,291 B2 | 4/2020 | Batchelor | |
| 2004/0097804 A1 | 5/2004 | Sobe | |
| 2011/0220479 A1 | 9/2011 | Zhou | |
| 2012/0101370 A1 | 4/2012 | Razzaque et al. | |
| 2013/0178852 A1 | 7/2013 | Allen, IV et al. | |
| 2014/0046323 A1 * | 2/2014 | Payne ................ | A61B 18/1445 606/45 |
| 2014/0048397 A1 | 2/2014 | Sykes et al. | |
| 2016/0051275 A1 * | 2/2016 | Batchelor ............ | A61B 17/295 606/48 |
| 2018/0085157 A1 | 3/2018 | Batchelor et al. | |

FOREIGN PATENT DOCUMENTS

| | | |
|---|---|---|
| CN | 101516285 A | 8/2009 |
| CN | 104271061 A | 1/2015 |
| CN | 105682592 A | 6/2016 |
| CN | 107865687 A | 4/2018 |
| CN | 107865687 B | 11/2020 |
| WO | WO-2010077632 A2 | 7/2010 |
| WO | WO-2017052703 A1 | 3/2017 |
| WO | WO-2017052704 A2 | 3/2017 |

OTHER PUBLICATIONS

"Chinese Application Serial No. 201710880372.1, Office Action dated Feb. 28, 2020", with machine translation, 10 pgs.

"U.S. Appl. No. 15/701,934, Notice of Allowance dated Nov. 18, 2019", 8 pgs.

"Chinese Application Serial No. 201710880372.1, Voluntary Amendment Filed Jan. 3, 2020", with Machine Translation, 33 pgs.

U.S. Appl. No. 15/701,934 U.S. Pat. No. 10,610,291, filed Sep. 12, 2017, Reconfigurable Instrument.

"Chinese Application Serial No. 201710880372.1, Response filed Jul. 2, 2020 to Office Action dated Feb. 28, 2020", with machine translation, 28 pgs.

* cited by examiner

RECONFIGURABLE INSTRUMENT

CROSS-REFERENCE TO PRIORITY APPLICATIONS

This application is a Continuation of U.S. application Ser. No. 15/701,934, filed on Sep. 12, 2017, which claims the benefit of U.S. Provisional Application Ser. No. 62/399,615, filed on Sep. 26, 2016, the contents of which are incorporated herein by reference in their entireties.

FIELD

These teachings relate to a medical instrument, and more particularly to a medical instrument that is adapted to provide a modality based on a measured impedance, a determined position of a moveable member, or both.

BACKGROUND

Some medical instruments are equipped with one or more controls or mechanisms for applying, transmitting, or providing one or more modalities to an anatomical feature or site of interest. The modalities may be electrosurgical or non-electrosurgical. However, during a medical procedure, locating and actuating the one or more of the controls may be difficult, time consuming, and/or cumbersome.

For example, in some instances, the controls may be located outside of a surgeon's natural hand position or finger reach, which may undesirably require the surgeon to reposition their grip on the instrument and/or look away from the anatomical feature or site of interest to locate the controls. Additionally, or alternatively, in some instances, actuating one or more of the controls may cause the instrument to unintentionally move or shift in the surgeon's hand and/or cause the anatomical feature to move or slip from the instrument, which may cause damage to the anatomical feature or site of interest and/or may add additional time to the procedure.

Some instruments have several controls, each of which may be configured or adapted to provide a different modality. Learning and/or deciding what modality each control is configured or adapted to apply, transmit, or provide may confuse or frustrate a surgeon and/or may add additional time to the procedure. Another concern is that a surgeon may actuate the wrong control(s), which may apply, transmit, or provide an unintended modality, which may result in damage to the instrument, the anatomical feature, and/or a site of interest.

It may therefore be desirable to have a medical instrument that is adapted to apply, transmit, or provide one or more modalities without requiring a surgeon to search for and/or actuate one or more controls. For example, it may be desirable to have an instrument that is adapted to apply, transmit, and/or provide a particular modality when an instrument is reconfigured from one use configuration to another use configuration—for example, when the instrument is reconfigured from a forceps device to a cutting blade, or vice versa. It may be desirable to have an instrument that is enabled to apply, transmit, or provide a particular modality to an anatomical feature or site of interest when one or more moveable members are moved or repositioned—for example, when the arms of the instrument are positioned in a closed or open position; when an arm or blade is advanced or retracted; when a shuttle, switch or other control is moved; or a combination thereof.

Examples of some medical instruments may be found in U.S. Pat. Nos. 7,179,258 and 8,251,989; and in U.S. Patent Application Publication No. 2016/0051275A1, all of which are incorporated by reference herein for all purposes.

SUMMARY

These teachings relate to an instrument that may be adapted or configured to provide a particular modality without requiring a surgeon to search for and/or actuate one or more controls. For example, these teachings provide an instrument that is adapted to apply, transmit, and/or provide a particular modality when the instrument is reconfigured from one use configuration to another use configuration—for example, when the instrument is reconfigured from a forceps device to a cutting blade, or vice versa. These teachings provide an instrument where a particular modality can be applied, transmitted, or provided from the instrument to an anatomical feature or site of interest when one or more moveable members are moved or repositioned—for example, when the arms of the instrument are in a closed or open position; when an arm or blade is advanced or retracted; when a shuttle, switch or other control is activated; or a combination thereof.

These teachings relate to an instrument. The instrument may be a medical instrument. The instrument may include one or more passive circuit elements. An impedance of the passive circuit element(s) may be measured. The impedance may be measured by a power source, a controller, a computer, or a combination thereof. The measured impedance may be converted into a positional encoder or an encoder signal. The measured impedance may be converted into a positional encoder or an encoder signal by a power source, a controller, a computer, or a combination thereof. The positional encoder or encoder signal may be used to determine or resolve a position or location of the moveable member. The instrument may be enabled to provide a modality based on the determined or resolved position of the moveable member, the encoder signal, the measured impedance, or a combination thereof. The modality may be electrical or non-electrical.

The instrument disclosed herein may be a bipolar electrosurgical instrument having a pair of electrodes. The instrument may be a bipolar forceps. The instrument may include more than one pair of electrodes. The instrument may include a moveable member that includes one or more passive circuit elements and one or more corresponding terminals. Additionally, or alternatively, in some configurations, one or more passive circuit elements may be located on one or more of the arms. When the moveable member is moved so that the terminals are in electrical communication with one or more electrodes thus completing or closing an electrical circuit, an impedance of the passive circuit element in the completed electrical circuit is measured. The measured impedance is converted into an encoder signal. A position or location of the moveable member relative to the hand piece or one or more other features on the instrument is determined or resolved based on the encoder signal. The instrument may be adapted or configured to provide a particular modality based on the encoder signal; the determined position of the movable member; the determined, measured or resolved impedance; or a combination thereof. For example, based on the encoder signal, the determined position of the movable member, the determined, measured or resolved impedance, or a combination thereof, the instrument may be adapted or configured to provide a monopolar therapeutic current from one electrode to another; a bipolar therapeutic current from one electrode to another; or electrical current may cease to be provided to and from the instrument all together.

These teachings provide an instrument including working arms and a moveable member. The working arms include a first arm, a second arm, a first electrode located on the first arm, and a second electrode located on the second arm. The moveable member includes a passive circuit element, a first terminal, and a second terminal. The moveable member is moveable to a first position and a second position. In the first position, the first terminal is in electrical communication with the first electrode and the second terminal is in electrical communication with the second electrode so that in the first position an electrical circuit is completed. An impedance is measured of the passive circuit element in the completed electrical circuit. The instrument is adapted to provide a therapeutic modality based on the measured impedance.

An instrument comprising a pair of working arms and a moveable member comprising a terminal. The pair of working arms comprise: a first arm; a second arm; a first electrode located on the first arm; a second electrode located on the second arm; and a passive circuit element located on the first arm or the second arm. The moveable member is moveable to a first position and a second position. In the first position, the terminal is in electrical communication with both the first electrode and the second electrode so that in the first position an electrical circuit is completed, the completed electrical circuit comprising the passive circuit element, the first electrode, and the second electrode. An impedance is measured of the passive circuit element in the completed electrical circuit. The instrument is adapted to provide a therapeutic modality based on the measured impedance. In the second position, the terminal is free of electrical communication with at least one of the first electrode and the second electrode so that the electrical circuit is open.

DETAILED DESCRIPTION

Figure 1A:
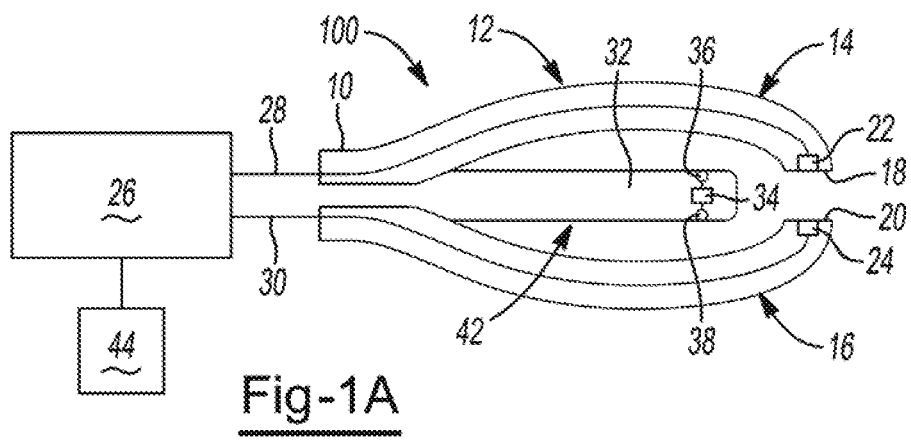
FIG. 1A is a cross-sectional view of an instrument having a moveable member.

This application claims the benefit of U.S. 62/399,615 filed on Sep. 26, 2016, the entire disclosure of which is hereby incorporated by reference for all purposes.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide an instrument. The instrument may be used in medical and/or non-medical procedures. The instrument may be any instrument for effecting an object, an anatomical feature, and/or a site of interest. Effecting may mean, for example, manipulating, engaging, moving, grasping, gripping, constricting, pushing, pulling, cutting, tearing, coagulating, sealing, cauterizing, dissecting, desiccating, fulgurating, or otherwise effecting an object, an anatomical feature, and/or a site of interest. The effecting may be with or without electricity (i.e., electrosurgical or non-electrosurgical). The anatomical feature may be any anatomical feature, such as a vessel, tissue, vein, artery, the like, or a combination thereof. In medical procedures, the instrument may be used in open procedures, laparoscopic procedures, or both. The instrument may be forceps. The instrument may be an electrosurgical forceps. The instrument may be bipolar electrosurgical forceps. The instrument may have a blade. The instrument may be reconfigurable so that the instrument can be used in one or more configurations. For example, the instrument may be forceps in one configuration, and a scalpel or blade in another configuration. The instrument can be an electrosurgical instrument in one configuration and a non-electrosurgical instrument in another configuration. The instrument may be reconfigurable while effecting an object or anatomical feature. For example, an object or anatomical feature may be effected while being grasped or held between the arms of the instrument, and then a blade of the instrument may be moved while the object or anatomical feature is grasped or held between the arms to further effect the object or anatomical feature.

The instrument may be used with a system. The system may include a power source and/or a controller. The instrument may be connected to a power source or controller that is adapted or configured to read or measure an impedance of one or more circuits, one or more circuit elements, between two or more electrodes, a passive circuit element, a closed electrical circuit, or a combination thereof. For example, the system may be of the type disclosed in U.S. Pat. No. 7,179,258, which is hereby incorporated by reference in its entirely for all purposes.

The instrument may include a hand piece. The hand piece may function to house, support, and/or contain the introducer, the effector, one or more arms, one or more moveable members, one or more therapy leads, one or more passive circuit elements, a controller, a power source, or a combination thereof. The hand piece may function to house, support, and/or contain the parts, components and/or mechanism required for operating, actuating, moving, reciprocating, opening, closing, retracting, extending, rotating, and/or otherwise manipulating the introducer, the effector, one or more arms, one or more moveable members, or a combination thereof. The hand piece may include sufficient controls for operating, actuating, moving, reciprocating, opening, closing, retracting, extending, rotating, and/or manipulating the introducer, the effector, the one or more arms, the one or more moveable members, or a combination thereof. The one or more controls may include one or more triggers, wheels, levers, buttons, knobs, shuttles, switches, moveable members, the like, or a combination thereof.

The instrument may include one or more introducers. The introducer may function to permit a portion of the instrument to be inserted into a site of interest, while a portion of the instrument remains outside of the site of interest. The site of interest may be a location in the anatomy of a patient. The introducer may be an elongated, tubular member that extends along a longitudinal axis between opposing proximal and distal ends. The proximal end of the introducer may be connected to the hand piece. The distal end may be inserted into a site of interest, the patient, or the anatomy. The introducer may be substantially straight; may include one or more angles, bends or arcs; or a combination thereof. The introducer may be substantially rigid; substantially flexible; substantially resilient; or a combination thereof. The introducer may be a tubular member.

The introducer may be connected to the hand piece (e.g., not moveable), and the effector, the moveable member, and/or the one or more arms may be movable relative to the introducer and/or the hand piece. Moving the effector, the moveable member, and/or the arms in a direction towards the hand piece may cause the introducer to apply a force to one or more force receiving sections on the effector or arms thereby causing the arms to move towards one another into a closed or gripping position. Moving the effector, the moveable member, and/or the arms in a direction away from the hand piece may cause the introducer to remove a force from the one or more force receiving section on the effector or arms thereby allowing the arms to resiliently move away from one another into an open, spaced apart relationship.

In other configurations, the effector may be moveably connected to the hand piece, and the effector, the moveable member, and/or the arms may be fixedly connected to the hand piece. In such cases, the introducer may be moved to apply or remove forces to or from force receiving sections to cause the arms or moveable member to move between a closed or open position, respectively. One or more of the passive circuit elements, terminals, electrodes, or a combination thereof may be located on the introducer (e.g., on an inner portion of the introducer, outer portion of the introducer, or both).

The instrument may include one or more effectors. The effector may be used to effect an object, a site of interest, and/or an anatomical feature. For example, the effector may permit holding, manipulating, engaging, moving, grasping, gripping, constricting, pushing, pulling, cutting, tearing, coagulating, sealing, cauterizing, dissecting, fulgurating, or a combination thereof an object, a site of interest, and/or an anatomical feature. The effector may be, or may include, one or more arms, blades, scalpels, electrodes, jaws, or a combination thereof. An electrical current may be applied from the effector to an object, site of interest, and/or anatomical feature.

The instrument may include one or more arms. The effector may include one or more arms. The one or more arms may be arms or jaws of a forceps. The one or more arms may cooperate to perform any of the functions of a forceps instrument. The one or more arms may be adapted or configured to effect an object, a site of interest, and/or an anatomical feature. For example, the one or more arms may be used for manipulating, engaging, moving, grasping, gripping, constricting, pushing, pulling, cutting, tearing, coagulating, sealing, cauterizing, dissecting, desiccating, fulgurating, or otherwise effecting an object, a site of interest, and/or an anatomical feature. The one or more arms may be adapted or configured to provide a clamping force to secure an object or anatomical feature; provide retraction of an object or anatomical feature; provide a compression or gripping force across an object or anatomical feature; or a combination thereof. The one or more arms may be moved, pivoted, flexed, and/or otherwise manipulated between an open configuration and a closed or gripping configuration.

The one or more arms may be made of any material suitable for use in medical procedures. For example, the one or more arms may be made of steel, stainless steel, carbon steel, or a combination thereof. The one or more arms may be electrically conductive so that an electrical signal or current can be passed to, from, and/or between the arms. The one or more arms (or parts of one or more arms) may be electrically insulated so that an electrical signal or current is prevented from being passed from one arm or jaw to another arm or jaw. The one or more arms are made from a material that can withstand repeated sterilization in high-temperature autoclaves. However, the arms may also be made of material intended to be used once and then discarded. The one or more arms may be substantially straight; may include one or more angles, bends or arcs; or a combination thereof. The one or more arms may be substantially rigid; substantially flexible; substantially resilient; or a combination thereof. The one or more arms may include one or more jaws, one or more electrodes, one or more passive circuit elements, one or more terminals, one or more therapy leads, one or more nodes, or a combination thereof.

The instrument may include one or more jaws. The effector may include one or more jaws. The one or more arms may include one or more jaws. The one or more jaws may function to effect an object, a site of interest, and/or an anatomical feature. For example, the one or more jaws may be used for manipulating, engaging, moving, grasping, gripping, constricting, pushing, pulling, cutting, tearing, coagulating, sealing, cauterizing, dissecting, desiccating, fulgurating, or otherwise effecting an object, a site of interest, and/or an anatomical feature. The one or more jaws may comprise a surface (i.e., a gripping or effecting surface) to grip an object, a site of interest, and/or an anatomical feature. For instance, the one or more jaws may be at least partially smooth, flat, contoured, serrated, textured, horizontal, vertical, planar, canted, rolling, irregular, or a combination thereof. The one or more jaws may include one or more ridges, mouse teeth, gaps, openings, of a combination thereof. The one or more jaws may be electrically conductive so that a therapy current can be passed there through, or the one or more jaws may be electrically insulated so that a therapy current is prevented from being passed. The one or more jaws may include one or more electrodes, one or more terminals, one or more passive circuit elements, or a combination thereof.

The instrument may include one or more electrodes. The effector may include one or more electrodes. The arms may include one or more electrodes. The jaws may include one or more electrodes. The moveable member may include one or more electrodes. The one or more electrodes may be located long an entire length of one or more of the effector, arms, blades, moveable members, and/or jaws. The one or more electrodes may be located in one or more discrete areas of one more of the arms, blades, moveable member, and/or jaws, such as at a distal tip thereof. The one or more electrodes may be electrically connected to a power source, a controller, one or more passive circuit elements, via one or more therapy leads, conductors, conductor wires, or a combination thereof. The one or more electrodes may be therapeutic electrodes or non-therapeutic electrodes.

The one or more electrodes may be therapeutic electrodes that may function to electrically effect an object, a site of interest, and/or an anatomical feature. For example, the one or more therapeutic electrodes may function to manipulate, engage, move, grasp, grip, constrict, push, pull, cut, tear, coagulate, seal, cauterize, dissect, desiccate, fulgurate, or otherwise electrically effect an object, a site of interest, and/or an anatomical feature. The one or more therapeutic electrodes may function to electrically effect an object, a site of interest, and/or an anatomical feature with one or more electrical modalities. For example, the one or more therapeutic electrodes may function to electrically effect an object, a site of interest, and/or an anatomical feature with a bipolar therapy current, a monopolar therapy current, or a blended bipolar and monopolar therapy current. The one or more therapeutic electrodes may make direct contact or engage an object, anatomical feature, and/or a site of interest. The one or more therapeutic electrodes may be connected to a power source via one or more therapy leads or conductor wires. Each therapeutic electrode may be connected to the power source with a discrete therapy lead or conductor; two or more electrodes may be connected to the power source via a common therapy lead or conductor; or a combination thereof.

One or more of the electrodes may be a non-therapeutic electrode. A non-therapeutic electrode may be an electrode, or an area of a therapeutic electrode, that is not used for effecting an object, a site of interest, and/or an anatomical feature. For example, a non-therapeutic electrode may be an electrode or part of an electrode that does not make direct contact with an object, anatomical feature, or site of interest. A non-therapeutic electrode may be used for completing an electrical circuit; measuring or obtaining an impedance reading across one or more circuits; measuring or obtaining an impedance of a passive circuit element located in one or more completed or closed circuits, or a combination thereof. A non-therapeutic electrode may provide a more reliable measurement or connection area than a therapeutic electrode because the non-therapeutic electrodes may be unaffected or not-covered in charred tissue, carbon buildup, etc. from effecting an object, a site of interest, and/or an anatomical feature like therapeutic electrodes may be. Non-therapeutic electrodes may be located away from an object, a site of interest, and/or an anatomical feature so that the non-therapeutic electrode remains clean and unaffected by effecting procedures or events. For example, the non-therapeutic electrode(s) may be located proximal of the therapeutic electrodes. The non-therapeutic electrodes may be located on the arms or jaws, but closer to the hand piece compared to the therapeutic electrodes. The non-therapeutic electrodes may be located in the hand piece, while the therapeutic electrodes are located in the effector, the arms, the jaws, or a combination thereof.

An impedance of one or more of the electrodes may be monitored and/or measured by the power source, the controller or both. The impedance of one or more electrodes may be monitored and/or measured when one or more electrical circuits are open or closed. The impedance of one or more electrodes may be monitored and/or measured while an object or anatomical feature is surgically effected so that when the impedance reaches a certain level, an electrical current or modality is reduced or eliminated.

The instrument may include one or more therapy leads. The one or more therapy leads may function to electrically interconnect the instrument, a power source, one or more electrodes, one or more passive circuit elements, one or more terminals, a controller, or a combination thereof. The one or more therapy leads may be one or more conductors, leads, or conductor wires that may function to, or be adapted to, transmit one or more electrical signals, modalities, therapy signals, impedance measurements, encoders, encoder signals, or a combination thereof between the instrument, a power source, the one or more electrodes, one or more passive circuit elements, a controller, or a combination thereof. The one or more therapy leads may be insulated to prevent accidental arcing or shorting between the power source and the electrodes.

A terminal as used herein may be an electrical conductor or node for electrically connecting to another element in a circuit, such as an electrode or therapy lead. A terminal may be an end of a single conductor (i.e., wire) that is used to electrically connect to another element. A terminal may be one or more plugs, pins, a pin, a socket, or any other electrical connector(s) or conductor(s) that is/are adapted to contact another element of the circuit, such as an electrode, passive circuit element, therapy lead, etc. to make an electrical connection therewith.

The instrument may include one or more nodes. The one or more nodes may be an area of a circuit comprising a conductor or therapy lead and two or more circuit elements. A node is a connection point of two or more conductors. The two or more circuit elements may be any combination of therapeutic electrodes, non-therapeutic electrodes, passive circuit elements, and the power source.

The instrument may include one or more circuits. The one or more circuits may include one or more of the circuit elements illustrated and/or described herein. For example, the one or more circuits may be defined by one or more therapy leads, electrodes, terminals, nodes, passive circuit elements, conductors, power sources, controllers, moveable members, or a combination thereof. The one or more circuits may be open or broken in a steady state configuration, and may be closed or completed when the moveable member is moved to a certain position, or vice versa.

A closed or completed circuit may mean electrical continuity across one or more elements of a circuit. For example, a closed or completed circuit may comprise electrical continuity across one or more electrodes, passive circuit elements, nodes, terminals, arms, jaws, therapy leads, generators, controllers, conductors, or a combination thereof. A closed or completed circuit may mean electrical power from a generator can be provided to one or more one or more electrodes, passive circuit elements, arms, jaws, therapy leads, terminals, nodes, controllers, or a combination thereof. The instrument may include more than one closed or completed circuit depending on the position of the moveable member When one or more circuits are closed or completed, an impedance may be measured or determined of one or more of the passive circuit elements and/or of that closed or completed circuit. The measured impedance may be converted into a positional encoder to determine or resolve a position of the moveable member. Depending on the measured impedance or the determined position of the moveable member, the instrument may be adapted to provide a modality or cease providing a modality. Depending on the measured impedance or the determined position of the moveable member, the instrument may be adapted, configured or enabled to provide a different modality than when the circuit is open or broken. For example, a monopolar, bipolar, or blended electrical current can be provided from the power source to the instrument or to one or more electrodes for effecting an object, site of interest, or anatomical feature. For example, electrical current can cease being provided from the power source to the instrument.

A broken or open circuit may mean electrical discontinuity between one or more elements of a circuit. For example, a broken or open circuit may mean that electrical power is unable to be provided to, across, or between one or more electrodes, passive circuit elements, arms, jaws, therapy leads, terminals, nodes, generators, controllers, or a combination thereof. When a circuit is broken or open, an impedance of that circuit and/or of the passive circuit element in that broken or open circuit is unable to be measured or determined.

When one or more circuits are open or broken, the instrument may be adapted, configured or enabled to provide a particular modality or cease providing a modality. When one or more circuits are open or broken, and an impedance of the circuit and/or one or more passive circuit elements is unable to be measured, the instrument may be adapted, configured or enabled to provide a different modality than when the circuit is closed or completed. For example, a monopolar, bipolar, or blended electrical current can be provided from the power source to the instrument or to one or more electrodes for effecting an object, site of interest, or anatomical feature. For example, electrical current can cease being provided from the power source to the instrument.

The instrument may include one or more moveable members. The moveable member may be enabled, configured, or adapted to open and/or close one or more electrical circuits. The moveable member may be moved to one or more positions (e.g., a first position, a second position, a third position, etc.), and depending on the position of the moveable member, a particular circuit may be opened or closed. The moveable member may be moved by moving or manipulating a control, such as a switch, knob, or shuttle on the hand piece with a finger or by hand, or by depressing a foot pedal.

The moveable member may be a blade. After the moveable member or blade is moved to a particular position, such as the first position, for example, a distal end of the moveable member or blade may project or extend beyond a distal end of the pair of working arms. After the moveable member or blade is moved to a different position, such as a second position, for example, the moveable member or blade may be retracted so that a distal end of the moveable member or blade does not extend beyond a distal end of the pair of working arms. The moveable member or blade may be moved to a position so that a distal end of the moveable member or blade is generally flush with a distal end of the pair of working arms. The moveable member may be one or more of the arms. The moveable member may be the one or more controls (i.e., switch, knob, or shuttle on the hand piece or a foot pedal).

The moveable member may include one or more circuit elements. For example, the one or more moveable members may include one or more conductors, wires, terminals, electrodes, passive circuit elements, or a combination thereof. The moveable member may be moved into one or more positions, and depending on the position of the moveable member the one or more conductors, wires, terminals, electrodes, passive circuit elements, or a combination thereof on the moveable member may open or close a circuit.

The instrument may include one or more passive circuit elements. The passive circuit element may function or be adapted to provide for an impedance measurement to be made or determined when an electrical circuit is completed closed. An impedance of the passive circuit element in a closed or completed circuit may be measured. The passive circuit element may comprise one or more RLC circuits. The passive circuit element may comprise one or more resistors, one or more capacitors, one or more inductors, or a combination thereof. The passive circuit element can be a rectifying circuit. The passive circuit element can be a diode. The passive circuit element may function to measure an impedance of a closed circuit. The passive circuit element may be adapted to measure an impedance of itself when part of a closed or completed circuit. The passive circuit element may function to convert the measured impedance into an encoder signal. The instrument may include more than one passive circuit element. The one or more passive circuit elements may each have an impedance that is different than another. The one or more passive circuit elements may be arranged in parallel or in series with one another.

The instrument may be in communication with one or more power sources. The power source may function to provide one or more electrosurgical modalities to the instrument, effector, the one or more electrodes, the one or more arms, the one or more jaws, the blade, the moveable member, or a combination thereof. The power source may function to measure an impedance of a closed circuit. The power source may function to measure an impedance of one or more passive circuit elements. The power source may function to convert the measured impedance into an encoder signal. The power source may be a generator. The power source may provide electrical energy to the instrument, the system, and/or one or more features of the instrument or system described herein. The power source may be an AC source. The power source may be a separate source that is connected to the instrument via one or more cables or therapy leads. For example, the power source may be of the type described in U.S. Pat. No. 7,282,048B2, the teachings of which are hereby incorporated by reference herein for all purposes. The power source may be a DC source. The power source may be contained in the hand piece of the instrument.

The controller may function to determine or measure an impedance of a passive circuit element, a closed or completed electrical circuit, or both. The controller may convert the determined or measured impedance into an encoder signal using a look up table that is stored in a memory. The controller may convert the determined or measured impedance into an encoder signal by solving or running one or more equations or algorithms. The controller may have a processor, a memory storage, or both. The controller may be a computer, processor, microprocessor, or a combination thereof. The controller may be in communication with the instrument, the power source, or both. The controller may be part of, or incorporated into, the power source. The controller may be part of the instrument, the moveable member, the effector, the passive circuit element, a closed electrical circuit, or a combination thereof. The controller may be a discrete device in communication with one or both of the instrument and the power source.

The measured or determined impedance of a closed circuit, a passive circuit element, or both may be converted into an encoder signal. The encoder signal may be a positional encoder signal. The encoder signal may be a rotational encoder signal. The encoder signal may be used to determine or resolve a position of the moveable member. The determined or resolved position of the moveable member may be used to provide one or more therapeutic modalities; cease providing one or more therapeutic modalities, or a combination thereof. The measured or determined impedance may be converted into an encoder signal via the controller, the power source, a computer, a processor, with a look-up table, or a combination thereof.

Depending on a determined position of the moveable member, a measured impedance of a closed circuit, the inability to measure an impedance of a circuit (i.e., an open circuit), or a combination thereof, the instrument is adapted to provide a particular modality or cease providing a modality.

The modality may be an electrosurgical modality where a current is provided from the generator to one or more electrodes, arms, jaws, blades, or a combination thereof. The electrosurgical modality may be a monopolar current, a bipolar current, or a blended monopolar and bipolar current.

The modality may be a non-electrical or non-electrosurgical modality.

A change in modality may occur depending on a determined position of the moveable member, a measured impedance of a closed circuit, the inability to measure an impedance of a circuit (i.e., an open circuit), or a combination thereof. For example, a bipolar current may be provided from the generator to the instrument, and once the moveable member is moved to a new position and the position of the moveable member is determined, a monopolar current may be provided to the instrument, or current may cease being provided to the instrument all together.

A modality or a change in modality may include various intensity levels of an electrical current, therapy, and/or signal. For example, a modality may include low power, medium power, high power, etc. A modality may be a low, medium, and/or high frequency setting. A modality may be in the form of a changed voltage, amplitude, power, current, frequency, or a combination thereof.

The figures of this disclosure illustrate exemplarity instruments and features, some of which have been described in this disclosure. It is understood that the instruments and features illustrated in a particular figure are not necessary limited to that one particular figure, instrument, feature, and/or embodiment. In other words, it is within the scope of this disclosure and it is understood that feature(s) illustrated and/or described in one figure can be added, replaced, combined, substituted and/or modified with feature(s) illustrated and/or described in other figures. Moreover, it is within the scope of this disclosure and it is understood that some features that are only described in the disclosure can be added, replaced, combined, substituted and/or modified with other features shown and/or described herein.

FIG. 1A illustrates an instrument 100. The instrument 100 comprises a hand piece 10 and an effector 12. The instrument 100 comprises a pair of working arms, comprising a first arm 14 and a second arm 16. The first arm 14 includes a first jaw 18, and the second arm 16 includes a second jaw 20. A first electrode 22 is located on the first arm 14, and a second electrode 24 is located on the second arm 16. The electrodes 22, 24 are in electrical communication with a power source 26 via respective therapy leads 28, 30. The instrument 100 comprises a moveable member 32. The moveable member 32 comprises a passive circuit element 34 and a pair of terminals 36, 38 that are in electrical communication with the passive circuit element 34.

Figure 1B:
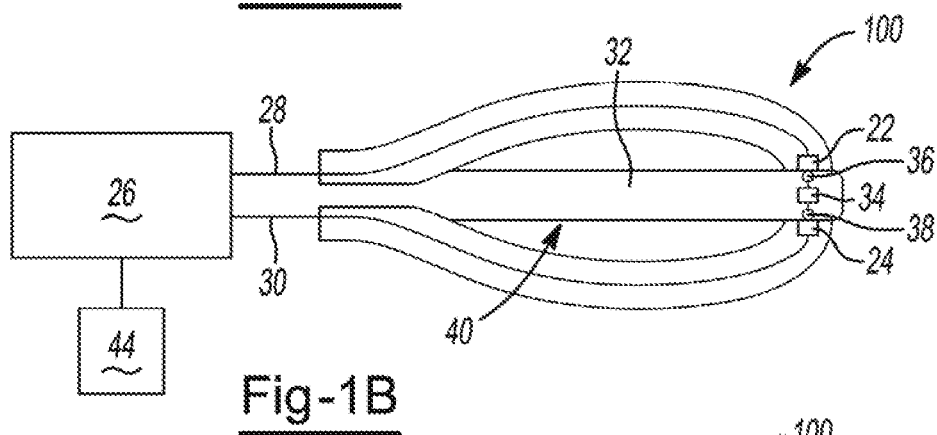
FIG. 1B is a cross-sectional view of the instrument of FIG. 1A with a moveable member in another position.

With additional reference to FIG. 1B, the moveable member 32 is moveable to a position 40 (FIG. 1B) and to a position 42 (FIG. 1A). In the position 40 (FIG. 1B), the terminals 36, 38 are in electrical communication with the corresponding first and second electrodes 22, 24 thus completing or closing an electrical circuit. The completed electrical circuit of FIG. 1B comprises the electrodes 22, 24, the terminals 36, 38, the passive circuit element 34, the therapy leads 28, 30, and the power source 26. A controller 44 is adapted or configured to measure an impedance of the passive circuit element 34 in the completed electrical circuit of FIG. 1B and/or measure an impedance of the entire completed electrical circuit of FIG. 1B. The measured impedance is converted into an encoder signal so that the position of the moveable member 32 is determined or resolved (e.g., that the moveable member is in position 40). The instrument 100 is adapted to provide a modality or cease providing a modality depending on the measured impedance, the encoder signal, the determined position 40 of the movable member 32, or a combination thereof. For example, when the moveable member 32 is determined to be in position 40, electrical current from the power source 26 may cease being provided to the electrodes 22, 24 so that the instrument 100 can be used as a cold-cut or non-electrosurgical cutting blade or as non-electrosurgical forceps.

When the moveable member 32 is moved to position 42 (FIG. 1A), one or both of the terminals 36, 38 are electrically disconnected or not in electrical communication with the corresponding first and second electrodes 22, 24. Thus, the electrical circuit that was illustrated and previously described in FIG. 1B is open or broken when the moveable member 32 is in the position 42. Accordingly, an impedance of the passive circuit element 34 in the open electrical circuit of FIG. 1A and/or an impedance of the open electrical circuit in FIG. 1A is unable to be measured. However, a controller 44 may be able to determine the position 42 of the moveable member 32 based on the inability to measure an impedance of the passive circuit element 34 and/or the inability to measure an impedance of the now open electrical circuit of FIG. 1A. The instrument 100 may be adapted to provide a modality or cease providing a modality based on this determined position 42 of the moveable member 32, the inability to measure the impedance of the passive circuit element 34 and/or the now open electrical circuit, or a combination thereof. For example, when the moveable member 32 is determined to be in position 42, electrical current from the power source 26 may be provided to the electrodes 22, 24 so that the instrument 100 can be used as an electrosurgical forceps. For example, when the moveable member 32 is determined to be in position 42, electrical current from the power source 26 may cease to be provided to the electrodes 22, 24 so that the instrument 100 can be used as a non-electrosurgical forceps.

Figure 2:
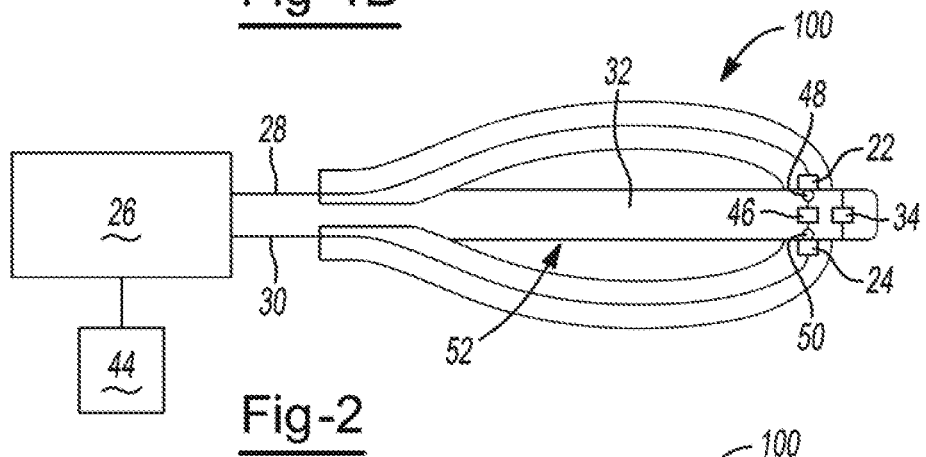
FIG. 2 is a cross-sectional view of an instrument having a moveable member.

FIG. 2 illustrates an instrument 100. The instrument 100 of FIG. 2 may include one or more of the elements illustrated and described in FIGS. 1A and/or 1B. In addition to those elements, the moveable member 32 of FIG. 2 includes another passive circuit element 46 (i.e., "a second passive circuit element") and a pair of terminals 48, 50 in electrical communication with the second passive circuit element 46. The second passive circuit element 46 may have or may generate an impedance that is different than an impedance of the passive circuit element 34 described in FIGS. 1A and 1B. The moveable member 32 is moveable to a position 52. In position 52, the terminals 48, 50 are in electrical communication with the corresponding first and second electrodes 22, 24 thus completing or closing an electrical circuit. The completed electrical circuit of FIG. 2 comprises the electrodes 22, 24, terminals 48, 50, the second passive circuit element 46, the therapy leads 28, 30, and the power source 26. A controller 44 in communication with the power source 26 is adapted or configured to measure an impedance of the second passive circuit element 46 in the completed electrical circuit of FIG. 2 and/or measure an impedance of the completed electrical circuit of FIG. 2. The measured impedance is converted into an encoder signal so that the position 52 of the moveable member 32 is determined. The instrument 100 is adapted to provide a modality or cease providing a modality depending on the measured impedance of the second passive circuit element 46, an impedance of the closed or completed circuit of FIG. 2, the encoder signal, the determined position 52 of the movable member 32, or a combination thereof. For example, when the moveable member 32 is determined to be in position 52, electrical current from the power source 26 may cease being provided to the electrodes 22, 24 so that the instrument 100 can be used as a cold-cut blade or a non-electrosurgical blade, or as non-electrosurgical forceps. For example, when the moveable member 32 is determined to be in position 52, electrical current from the power source 26 may be provided to the electrodes 22, 24 so that the instrument 100 can be used as an electrosurgical blade.

Figure 3:
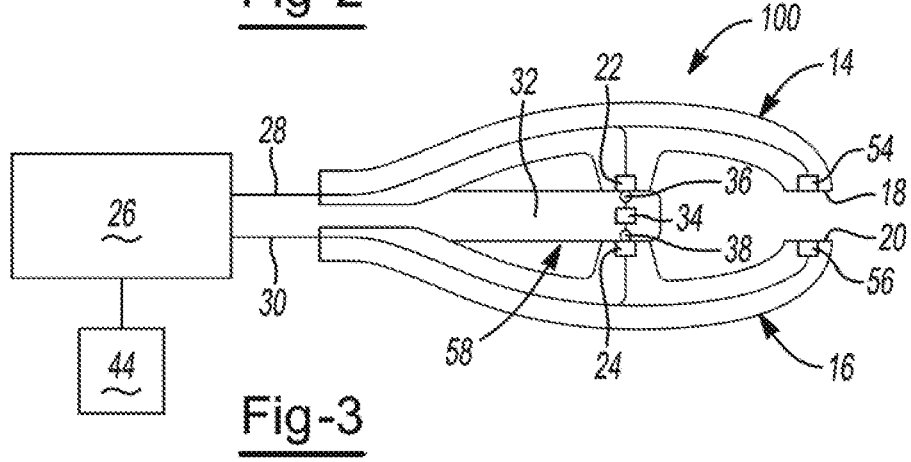
FIG. 3 is a cross-sectional view of an instrument having a moveable member.

FIG. 3 illustrates an instrument 100. The instrument 100 of FIG. 3 may include one or more of the features illustrated and described in FIGS. 1A, 1B, 2. In addition to those elements, the instrument 100 comprises a third electrode 54 located on the first arm 14, and a fourth electrode 56 located on the second arm 16. Electrodes 54, 56 may be therapeutic electrodes for effecting an object, anatomical feature and/or site of interest. Electrodes 22, 24 may be non-therapeutic electrodes. Electrodes 22, 54 are electrically connected in series and in electrical communication with a power source 26 via therapy lead 28. Electrodes and 24, 56 are electrically connected in series and in electrical communication with the power source 26 via therapy lead 30. The instrument 100 includes a moveable member 32. The moveable member 32 comprises a passive circuit element 34. The moveable member 32 is moveable to a position 58 where the terminals 36, 38 are in electrical communication with the corresponding first and second electrodes 22, 24 thus completing or closing an electrical circuit. The completed electrical circuit of FIG. 3 comprises the electrodes 22, 24, the terminals 36, 38, the passive circuit element 34, the therapy leads 28, 30, and the power source 26. Controller 44 is adapted or configured to measure an impedance of the passive circuit element 34 in the completed electrical circuit of FIG. 3 and/or measure an impedance of the completed electrical circuit of FIG. 3. The measured impedance is converted into an encoder signal so that the position 58 of the moveable member 32 is determined. The instrument 100 is adapted to provide a modality or cease providing a modality depending on the measured impedance of the passive circuit element 34 and/or an impedance of the closed circuit, the encoder signal, the determined position 58 of the movable member 32, or a combination thereof. For example, when the moveable member 32 is determined to be in position 58, electrical current from the power source 26 may cease being provided to the instrument 100 so that the instrument 100 can be used as non-electrosurgical forceps. For example, when the moveable member 32 is determined to be in position 58, electrical current from the power source 26 may be provided to the instrument 100 so that the instrument 100 can be used as an electrosurgical forceps and effect an object, anatomical feature, and/or site of interest with the therapeutic electrodes 54, 56. The non-therapeutic electrodes 22, 24 may be used strictly for completing the circuit so that an impedance of the passive circuit element 34 is read in the closed circuit.

With continued reference to FIG. 3, while not shown, the moveable member 32 is moveable to a position where the therapy leads 28, 30 are electrically disconnected from at least one of the electrodes 22, 24 so that the previously described electrical circuit is now open or broken. The controller 44 may be unable to measure an impedance of the passive circuit element 34 in this broken or open electrical circuit and/or may be unable to measure an impedance of the broken or open electrical circuit. However, the controller 44 may still be able to determine a position of the moveable member 32 based on the inability to measure an impedance of the passive circuit element 34 and/or the inability to measure an impedance of the now open electrical circuit. The instrument 100 may be adapted to provide a modality or cease providing a modality based on this determined position of the moveable member 32, the inability to measure the impedance of the passive circuit element 34 and/or the now open electrical circuit, or a combination thereof.

Figure 4A:
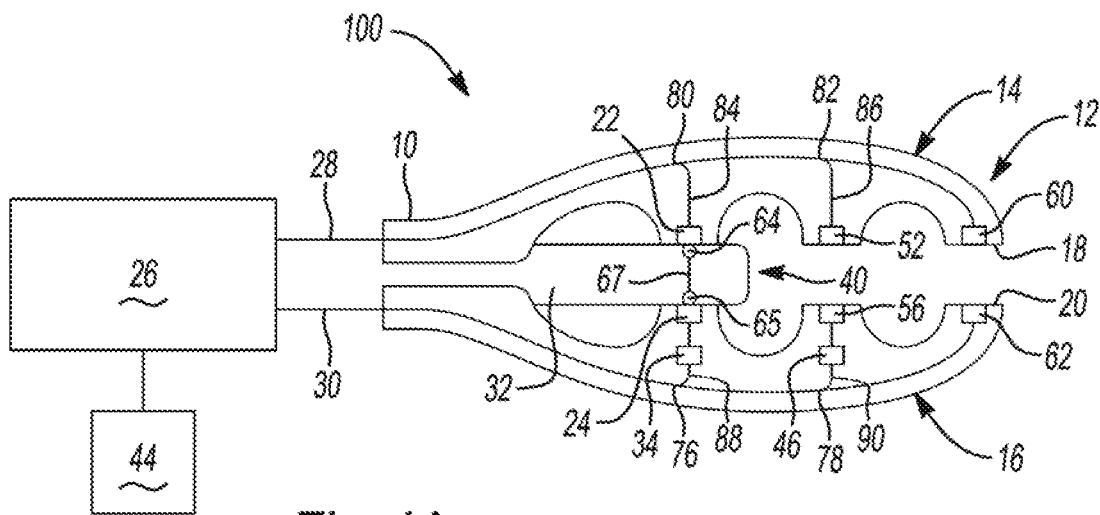
FIG. 4A is a cross-sectional view of an instrument having a moveable member.

FIG. 4A illustrates an instrument 100. The instrument 100 comprises a hand piece 10 and an effector 12. The instrument 100 comprises a pair of working arms, comprising a first arm 14 and a second arm 16. The first arm 14 includes a first jaw 18, and the second arm 16 includes a second jaw 20. A first electrode 22 is located on the first arm 14, and a second electrode 24 is located on the second arm 16. A third electrode 52 is located on the first arm 14, and a fourth electrode 56 is located on the second arm 16. A fifth electrode 60 is located on the first arm 14, and a sixth electrode 62 is located on the second arm 16. Electrodes 22, 52, 24, and 56 may be non-therapeutic electrodes, and electrodes 60, 62 may be therapeutic electrodes for effecting an object, anatomical feature, and/or site of interest. Electrodes 22, 52, and 60 may be electrically connected in series and are in electrical communication with a power source 26 via therapy lead 28. Electrodes 24, 56, and 62 may be electrically connected in series and are in electrical communication with the power source 26 via therapy lead 30. The second arm 16 includes a first passive circuit element 34 and a second passive circuit element 46. The first passive circuit element 34 has an impedance that is different than an impedance of the second passive circuit element 46. It is understood that one or both of the passive circuit elements 34, 46 can be located on the opposing first arm 14. The instrument comprises a first node 76, which includes the power source 26 and the passive circuit element 34; a second node 78 comprising the power source 26 and the passive circuit element 46; a third node 80 comprising the power source 26 and electrode 22; a fourth node 82 comprising power source 26 and electrode 52. The instrument also includes a conductor or lead 84 extending from line 28 to electrode 22; a conductor or lead 86 extending from line 28 to electrode 52; a conductor or lead 88 extending from line 30 to element 34; and a conductor or lead 90 from line 30 to element 46. The instrument 100 comprises a moveable member 32. The moveable member 32 comprises a first terminal 64, a second terminal 65, and a conductor 67 extending between the terminals 64, 65.

Figure 4B:
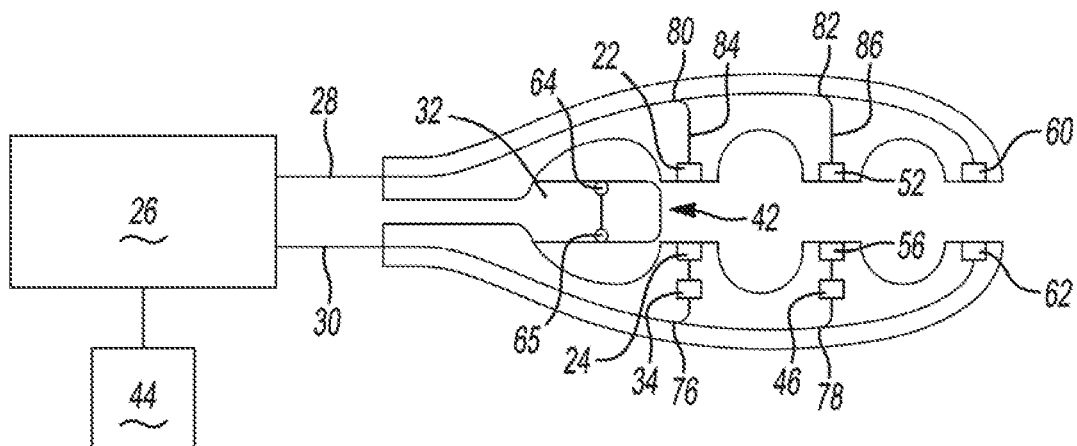
FIG. 4B is a cross-sectional view of the instrument of FIG. 4A with a moveable member in another position.

With additional reference to FIG. 4B, the moveable member 32 is moveable to a position 40 (FIG. 4A) and to a position 42 (FIG. 4B). In the position 40, the first terminal 64 is in electrical communication with the first electrode 22, and the second terminal 65 is in electrical communication with the second electrode 24 thus completing or closing an electrical circuit. The completed electrical circuit of FIG. 4A comprises the electrodes 22, 24, the terminals 64, 65, the conductor 67, the therapy leads 28, 30, and the first node 76 which comprises the passive circuit element 34 and the power source 26. A controller 44 is adapted or configured to measure an impedance of the passive circuit element 34 in the completed electrical circuit, and/or to measure an impedance of the completed electrical circuit in FIG. 4A. The measured impedance is converted into an encoder signal so that the position of the moveable member 32 is determined. The instrument 100 is adapted to provide a modality or cease providing a modality depending on the measured impedance, the encoder signal, the determined position 40 of the movable member 32, or a combination thereof. For example, when the moveable member 32 is determined to be in position 40, electrical current from the power source 26 may cease being provided to the instrument 100 so that the instrument 100 can be used as non-electrosurgical forceps. For example, when the moveable member 32 is determined to be in position 40, electrical current from the power source 26 may be provided to the instrument 100 so that the instrument 100 can be used as an electrosurgical forceps and effect an object, anatomical feature, and/or site of interest with the therapeutic electrodes 60, 62. The non-therapeutic electrodes 22, 24 and 52, 56 may be used strictly for completing the circuit so that an impedance of the respective passive circuit element 34, 46 is read in the closed circuit.

In position 42 (FIG. 4B), one or both of the terminals 64, 65 are free of electrical communication with a corresponding electrode 22, 24 or 52, 56. Accordingly, in the position 42, the electrical circuit shown and described in FIG. 4A is now open or broken. An impedance of the passive circuit element 34, or 46 and/or of any completed electrical circuit is unable to be measured. However, a controller 44 may still be able to determine a position 42 of the moveable member 32 based on the inability to measure an impedance of the passive circuit element 34, 46 and/or the inability to measure an impedance of the now open electrical circuit of FIG. 4B. The instrument 100 may be adapted to provide a modality or cease providing a modality based on this determined position 42 of the moveable member 32, the inability to measure the impedance of the passive circuit element 34, 46 and/or the now open electrical circuit, or a combination thereof.

Figure 4C:
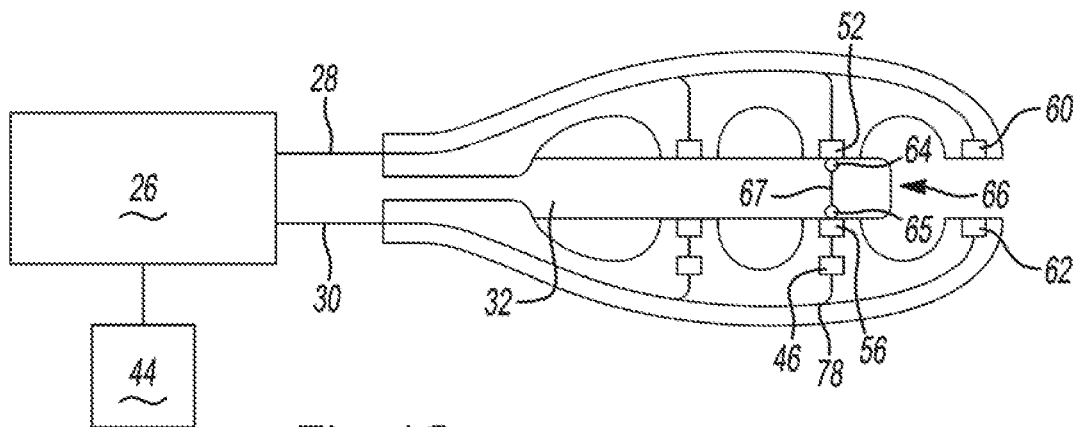
FIG. 4C is a cross-sectional view of the instrument of FIG. 4A with a moveable member in another position.

With additional reference to FIG. 4C, the moveable member 32 is moveable to another position 66. In the position 66 illustrated in FIG. 4C, the terminals 64, 65 are in electrical communication with the corresponding third and fourth electrodes 52, 56 thus completing or closing another electrical circuit. The completed electrical circuit of FIG. 4C comprises the electrodes 52, 56, terminals 64 and 65, conductor 67, the therapy leads 28, 30, and the second node 78 which comprises the passive circuit element 46 and the power source 26. A controller 44 (FIG. 4A) is adapted or configured to measure an impedance of the passive circuit element 46 in the completed electrical circuit of FIG. 4C and/or measure an impedance of the completed electrical circuit of FIG. 4C. The measured impedance is converted into an encoder signal so that the position 66 of the moveable member 32 is determined. The instrument 100 is adapted to provide a modality or cease providing a modality depending on the measured impedance, the encoder signal, the determined position 66 of the movable member 32, or a combination thereof. For example, when the moveable member 32 is determined to be in position 66, electrical current from the power source 26 may cease being provided to the instrument 100 so that the instrument 100 can be used as non-electrosurgical forceps. For example, when the moveable member 32 is determined to be in position 66, electrical current from the power source 26 may be provided to the instrument 100 so that the instrument 100 can be used as an electrosurgical forceps and effect an object, anatomical feature, and/or site of interest with the therapeutic electrodes 60, 62. The non-therapeutic electrodes 22, 24 and 52, 56 may be used strictly for completing the circuit so that an impedance of the respective passive circuit element 34, 46 is read in the closed circuit.

Figure 5A:
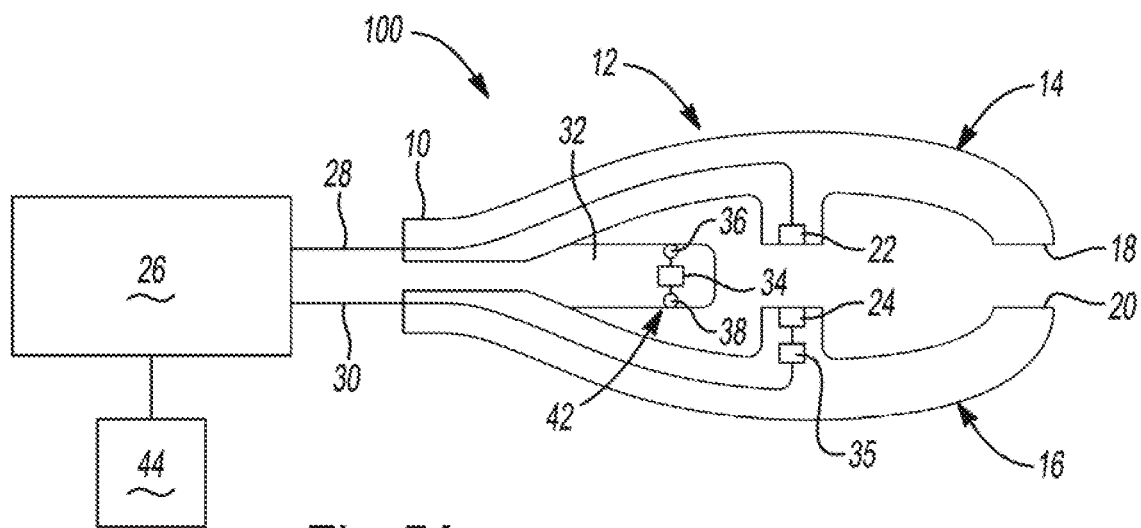
FIG. 5A is a cross-sectional view of an instrument having a moveable member.

FIG. 5A illustrates an instrument 100. The instrument 100 comprises a hand piece 10 and an effector 12. The instrument 100 comprises a pair of working arms, comprising a first arm 14 and a second arm 16. The first arm 14 includes a first jaw 18, and the second arm 16 includes a second jaw 20. A first electrode 22 is located on the first arm 14, and a second electrode 24 is located on the second arm 16. The electrodes 22, 24 are in electrical communication with a power source 26 via respective therapy leads 28, 30. The instrument 100 comprises a moveable member 32 that comprises a passive circuit element 34 and a pair of terminals 36, 38, each of which are in electrical communication with the passive circuit element 34. The second arm 16 includes a second passive circuit element 35; however, it is understood that the passive circuit element 35 can instead be located on the first arm 14.

Figure 5B:
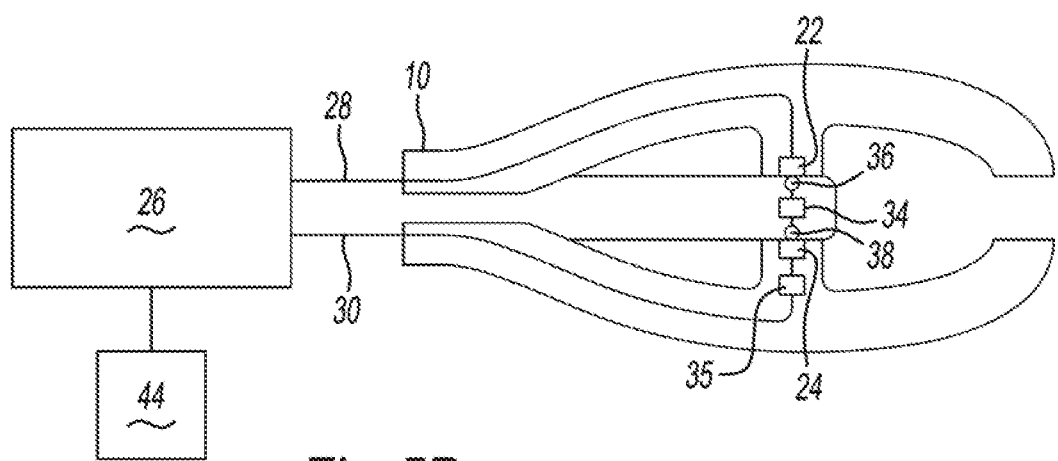
FIG. 5B is a cross-sectional view of the instrument of FIG. 5A with a moveable member in another position

With additional reference to FIG. 5B, the moveable member 32 is moveable to position 40 (FIG. 5B) and to a position 42 (FIG. 5A). In position 40 (FIG. 5B), the terminals 36, 38 are in electrical communication with the corresponding first and second electrodes 22, 24 thus completing or closing an electrical circuit. The completed electrical circuit of FIG. 5B comprises the electrodes 22, 24, the terminals 36, 38, the passive circuit element 34, the passive circuit element 35, the therapy leads 28, 30, and the power source 26. A controller 44 is adapted or configured to measure an impedance of the passive circuit elements 34, 35, which are arranged in series, in the completed electrical circuit, and/or measure an impedance of the completed electrical circuit in FIG. 5B. The measured impedance is converted into an encoder signal so that the position 40 of the moveable member 32 is determined. The instrument 100 is adapted to provide a modality or cease providing a modality depending on the measured impedance, the encoder signal, the determined position 40 of the movable member 32, or a combination thereof. For example, when the moveable member 32 is determined to be in position 40, electrical current from the power source 26 may cease being provided to the electrodes 22, 24 so that the instrument 100 can be used as non-electrosurgical forceps with jaws 18, 20. For example, when the moveable member 32 is determined to be in position 40, electrical current from the power source 26 may be provided to the electrodes 22, 24 so that the instrument 100 can be used as an electrosurgical blade.

When the moveable member 32 is moved to the position 42 (FIG. 5A), one or both of the terminals 36, 38 are not in electrical communication with the corresponding first and second electrodes 22, 24. Accordingly, in position 42, the electrical circuit that was illustrated and previously described in FIG. 5B is open or broken. An impedance of the passive circuit elements 34, 35 and/or the open electrical circuit is unable to measured. However, a controller 44 may still be able to determine a position 42 of the moveable member 32 based on the inability to measure an impedance of the passive circuit elements 34, 35 and/or the inability to measure an impedance of the now open electrical circuit of FIG. 5B. The instrument 100 may be adapted to provide a modality or cease providing a modality based on this determined position 42 of the moveable member 32, the inability to measure the impedance of the passive circuit elements 34, 35 and/or the now open electrical circuit, or a combination thereof. For example, when the moveable member 32 is determined to be in position 42, electrical current from the power source 26 may cease being provided to the electrodes 22, 24 so that the instrument 100 can be used as non-electrosurgical forceps. For example, when the moveable member 32 is determined to be in position 42, electrical current from the power source 26 may be provided to the electrodes 22, 24 so that the instrument 100 can be used as an electrosurgical blade.

Figure 6A:
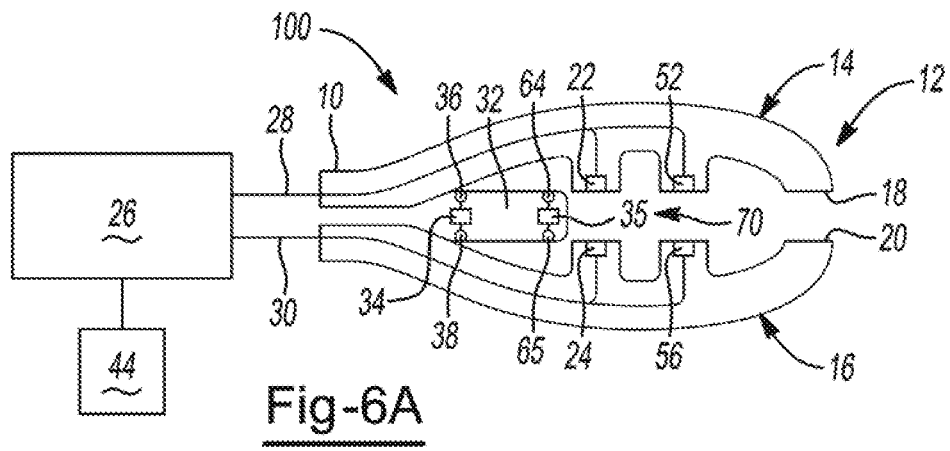
FIG. 6A is a cross-sectional view of an instrument having a moveable member.

FIG. 6A illustrates an instrument 100. The instrument 100 comprises a hand piece 10 and an effector 12. The instrument 100 comprises a pair of working arms, comprising a first arm 14 and a second arm 16. The first arm 14 includes a first jaw 18, and the second arm 16 includes a second jaw 20. A first electrode 22 is located on the first arm 14, and a second electrode 24 is located on the second arm 16. A third electrode 52 is located on the first arm 14, and a fourth electrode 56 is located on the second arm 16. Electrodes 22, 52 are electrically connected in series via conductor 28, and electrodes 24, 56 are electrically connected in series via conductor 30. Electrodes 22, 52 and 24, 56 are in electrical communication with a power source 26 via the respective therapy leads 28, 30. The instrument 100 comprises a moveable member 32. The moveable member 32 comprises a first passive circuit element 34 and a pair of terminals 36, 38, each of which are in electrical communication with the passive circuit element 34. The moveable member 32 also comprises a second passive circuit element 35 and a pair of terminals 64, 65, each of which are in electrical communication with the passive circuit element 35. An impedance of the first passive circuit element 34 is different than an impedance of the second passive circuit element 35.

Figure 6B:
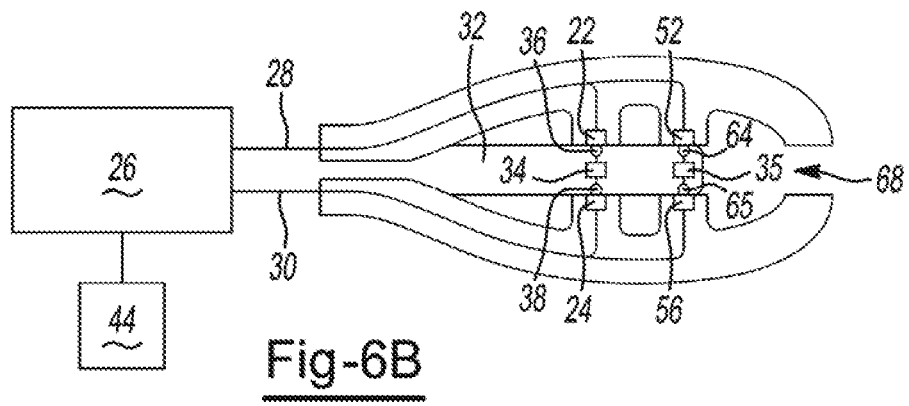
FIG. 6B is a cross-sectional view of the instrument of FIG. 6A with a moveable member in another position.

With additional reference to FIG. 6B, the moveable member 32 is moveable to position 68 (FIG. 6B) and to position 70 (FIG. 6A). In position 68 (FIG. 6B), terminals 36, 38 are in electrical communication with the corresponding first and second electrodes 22, 24, and terminals 64, 65 are in electrical communication with the corresponding third and fourth electrodes 52, 56 thus completing or closing an electrical circuit. The completed electrical circuit of FIG. 6B comprises the electrodes 22, 24, passive circuit element 34, terminals 36, 38, passive circuit element 35, terminals 64, 65, electrodes 52, 56, therapy leads 28, 30, and the power source 26. A controller 44 is adapted or configured to measure an impedance of the completed electrical circuit and/or the passive circuit elements 34, 35, which are arranged in parallel, in the completed electrical circuit of FIG. 6B and/or measure an impedance of the completed electrical circuit of FIG. 6B. The measured impedance is converted into an encoder signal so that the position 68 of the moveable member 32 is determined. The instrument 100 is adapted to provide a modality or cease providing a modality depending on the measured impedance, the encoder signal, the determined position of the movable member 32, or a combination thereof.

With continued reference to FIG. 6B, in position 68 the moveable member 32 completes closes two electrical circuits. The completed first electrical circuit comprises electrodes 22, 24, the terminals 36, 38, the passive circuit element 34, therapy leads 28, 30, and the power source 26; and the second completed circuit comprises electrodes 52, 56, terminals 64, 65, the passive circuit element 35, therapy leads 28, 30, and the power source 26. The first and second completed circuit are in parallel with each other.

In FIG. 6A, the moveable member is in position 70 where the previously described closed or completed circuit is now open. The controller 44 is unable to measure an impedance of the passive circuit elements 34, 35 and/or the now open or broken electrical circuit. However, a controller 44 may still be able to determine a position 70 of the moveable member 32 based on the inability to measure an impedance of the passive circuit elements 34, 35 and/or the inability to measure an impedance of the now open electrical circuits of FIG. 6A. The instrument 100 may be adapted to provide a modality or cease providing a modality based on this determined position 70 of the moveable member 32, the inability to measure the impedance of the passive circuit elements 34, 35 and/or the now open electrical circuits, or a combination thereof.

Figure 6C:
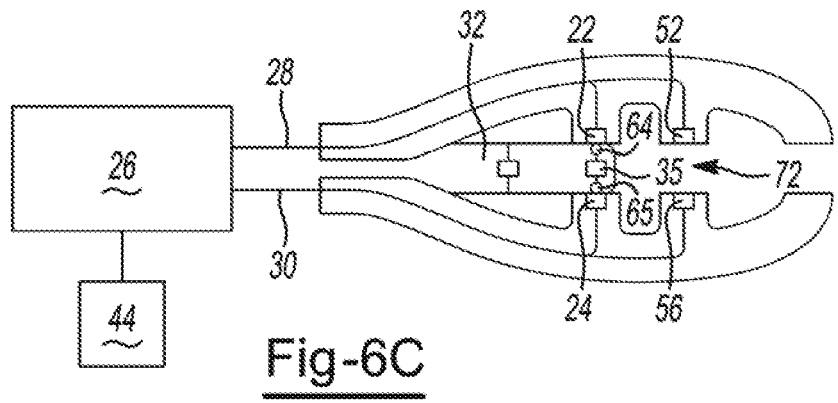
FIG. 6C is a cross-sectional view of the instrument of FIG. 6A with a moveable member in another position.

With additional reference to FIG. 6C, the moveable member 32 is moveable to position 72. In the position 72, the terminals 64, 65 are in electrical communication with the corresponding first and second electrodes 22, 24 thus completing or closing an electrical circuit. The completed electrical circuit of FIG. 6C comprises the electrodes 22, 24, terminals 64, 65, the passive circuit element 35, the therapy leads 28, 30, and the power source 26. A controller 44 is adapted or configured to measure an impedance of the passive circuit element 35 and/or the impedance of the completed electrical circuit of FIG. 6C. The measured impedance is converted into an encoder signal so that the position 72 of the moveable member 32 is determined. The instrument 100 is adapted to provide a modality or cease providing depending on the measured impedance, the encoder signal, the determined position 72 of the movable member 32, or a combination thereof.

Figure 6D:
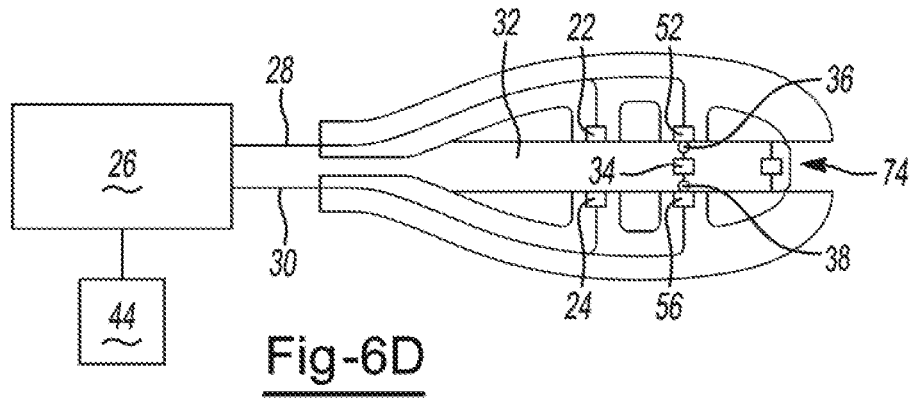
FIG. 6D is a cross-sectional view of the instrument of FIG. 6A with a moveable member in another position.

In FIG. 6D, the moveable member 32 is moveable to yet another position 74. In the position 74, the terminals 36, 38 are in electrical communication with the corresponding second and third electrodes 52, 56 thus completing or closing an electrical circuit. The completed electrical circuit of FIG. 6D comprises the electrodes 52, 56, terminals 36, 38, the passive circuit element 34, the therapy leads 28, 30, and the power source 26. The controller 44 is adapted or configured to measure an impedance of the passive circuit element 34 and/or an impedance of the completed electrical circuit of FIG. 6D. The measured impedance is converted into an encoder signal so that the position 74 of the moveable member 32 is determined. The instrument 100 is adapted to provide a modality or cease providing a modality depending on the measured impedance, the encoder signal, the determined position 74 of the movable member 32, or a combination thereof.

Figure 7:
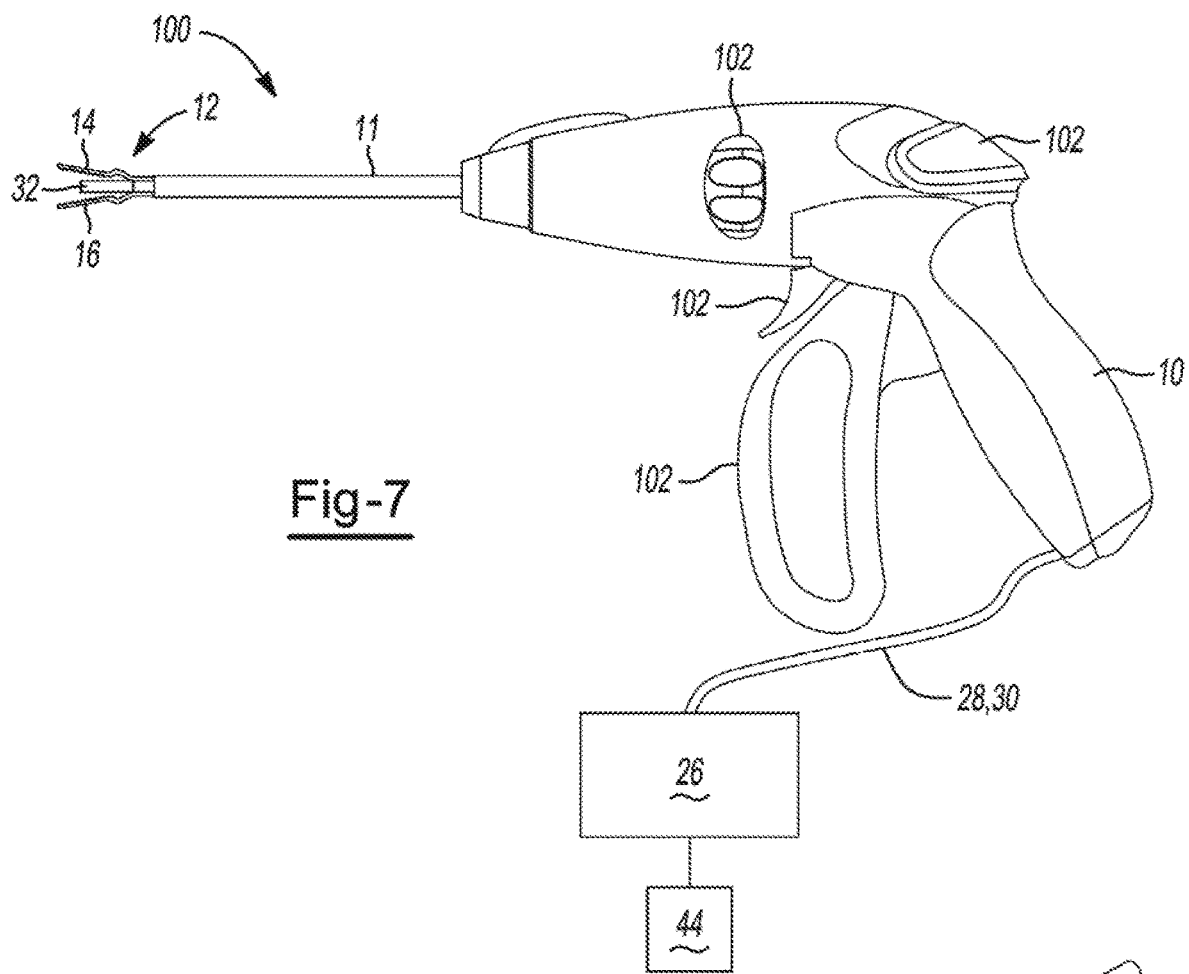
FIG. 7 is a side view of an instrument.

FIG. 7 illustrates an instrument 100. The instrument 100 includes a hand piece 10 and an effector 12. The instrument 100 includes a first arm 14 and a second arm 16. The instrument 100 includes one or more of the features illustrated and described in FIGS. 1A-6D. The instrument 100 is in electrical communication with a power source 26 and a controller 44 via therapy leads 28, 30. The instrument 100 includes a moveable member 32 that is illustrated as a blade. The instrument 100 includes one or more controls 102 for moving the moveable member 32. In addition, or alternatively, one or more of the controls 102 may be the moveable member 32.

Figure 8:
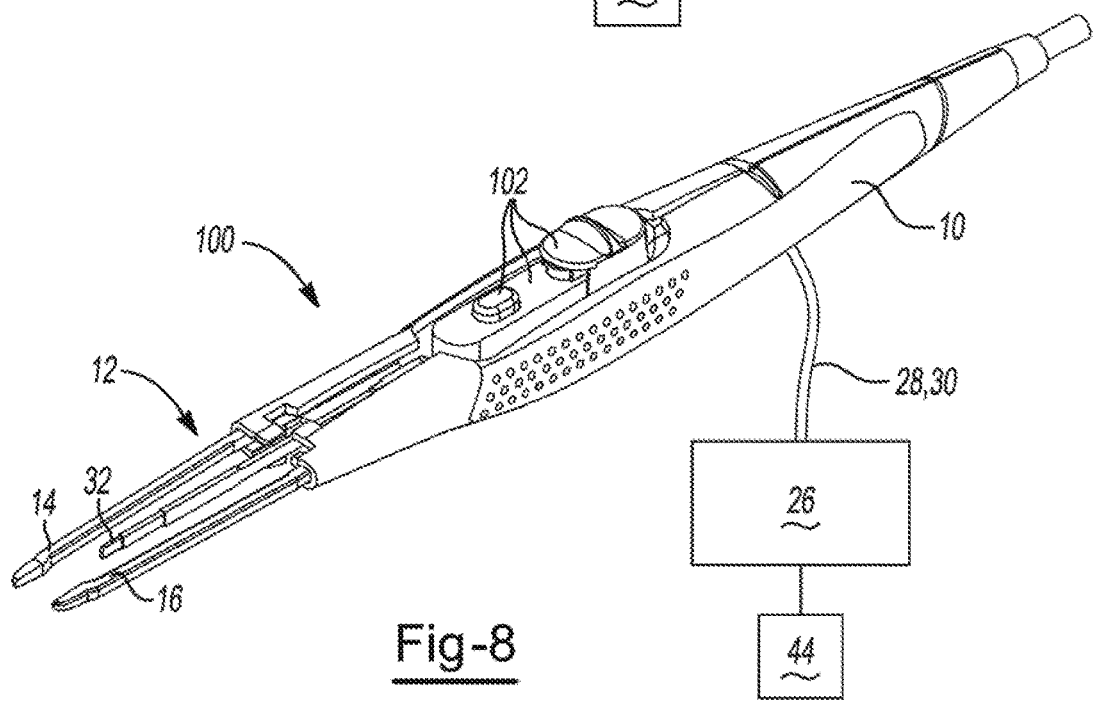
FIG. 8 is a perspective view of an instrument.

FIG. 8 illustrates an instrument 100. The instrument 100 includes a hand piece 10 and an effector 12. The instrument 100 includes a first arm 14 and a second arm 16. The instrument 100 includes one or more of the features illustrated and described in FIGS. 1A-6D. The instrument 100 is in electrical communication with a power source 26 and a controller 44 via therapy leads 28, 30. The instrument 100 includes a moveable member 32 that is illustrated as a blade. The instrument includes one or more 102 controls for moving the moveable member 32. In addition, or alternatively, one or more of the controls 102 may be the moveable member 32.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Teachings of a range in terms of at "'x' parts by weight of the resulting polymeric blend composition" also contemplates a teaching of ranges of same recited amount of "x" in percent by weight of the resulting polymeric blend composition.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. An instrument comprising:
a hand piece;
a pair of working arms comprising:
  i. a first arm;
  ii. a second arm;
  iii. a first electrode located on the first arm; and
  iv. a second electrode located on the second arm; and
a moveable member comprising:
  i. a passive circuit element;
  ii. a first terminal; and
  iii. a second terminal;
  wherein the moveable member is moveable to a first position and to a second position;
  wherein in the first position, the first terminal is in electrical communication with the first electrode and the second terminal is in electrical communication with the second electrode to form a completed electrical circuit;
  wherein in the second position, at least one of the first terminal and the second terminal is free of electrical communication with the respective first electrode and second electrode so that the electrical circuit is open; and
  wherein the moveable member is a shuttle that is located on the hand piece.

2. The instrument of claim 1, wherein the instrument is adapted to provide a modality when the moveable member is in the first position and the electrical circuit is completed.

3. The instrument of claim 2, wherein in the second position when the electrical circuit is open, the instrument is no longer adapted to provide the modality that is provided when the electrical circuit is completed.

4. The instrument of claim 2, wherein in the second position when the electrical circuit is open, the instrument is adapted to provide the modality.

5. The instrument of claim 2, wherein in the second position when the electrical circuit is open, the instrument is adapted to provide a second modality that is different than the modality provided when the electrical circuit is completed.

6. The instrument of claim 1, wherein the instrument is a bipolar electrosurgical forceps;
wherein the first electrode is a therapy electrode that is in electrical communication with a power source, and the second electrode is a therapy electrode that is in electrical communication with the power source, and
wherein in the second position, a therapy current from the power source is provided between the first electrode and the second electrode.

7. The instrument of claim 1, wherein the completed electrical circuit comprises the passive circuit element, and wherein a controller is configured to measure an impedance of the passive circuit element in the completed electrical circuit and convert the measured impedance into an encoder signal to determine that the moveable member is in the first position or in the second position.

8. The instrument of claim 1, wherein the completed electrical circuit comprises the passive circuit element, the first electrode, the second electrode, the first terminal, and the second terminal.

9. The instrument of claim 8, wherein an impedance is measured of the passive circuit element in the completed electrical circuit.

10. The instrument of claim 9, wherein the instrument is a bipolar electrosurgical forceps;
   wherein the pair of working arms comprise:
      v. a third electrode located on the first arm, the third electrode is a therapeutic electrode that is in electrical communication with a power source;
      vi. a fourth electrode located on the second arm, the fourth electrode is a therapeutic electrode that is in electrical communication with the power source;
      wherein the first electrode and the second electrode are each non-therapeutic electrodes to complete the electrical circuit when the moveable member is moved to the first position, and
      wherein the power source is adapted to provide a therapy current between the third electrode and the fourth electrode based on the measured impedance of the passive circuit element in the completed electrical circuit.

11. The instrument of claim 10, wherein the instrument comprises a first therapy lead that electrically connects both the first electrode and the third electrode with the power source, and
   wherein the instrument comprises a second therapy lead that electrically connects both the second electrode and the fourth electrode with the power source.

12. The instrument of claim 9, wherein the movable member comprises:
   a second passive circuit element;
   a third terminal; and
   a fourth terminal;
   wherein the moveable member is moveable to a third position;
   wherein in the third position, the third terminal is in electrical communication with the first electrode and the fourth terminal is in electrical communication with the second electrode so that a second electrical circuit is completed, the completed second electrical circuit comprises the second passive circuit element, the first electrode, the second electrode, the third terminal, and the fourth terminal;
   wherein an impedance is measured of the second passive circuit element in the completed second electrical circuit, the measured impedance of the second passive circuit element is different than the impedance of the passive circuit element; and
   wherein based on the measured impedance of the second passive circuit element, the instrument is enabled to determine that the moveable member is in the third position.

13. The instrument of claim 12, wherein the instrument is a bipolar electrosurgical forceps,
   wherein the first electrode is a therapy electrode that is in electrical communication with a power source, and the second electrode is a therapy electrode that is in electrical communication with the power source; and
   wherein in the third position, a therapy current based on the third position is provided from the power source to the first electrode and the second electrode.

14. The instrument of claim 13, wherein a controller is configured to measure the impedance of the second passive circuit element and convert the measured impedance of the second passive circuit element into an encoder signal to determine that the moveable member is in the third position.

15. The instrument of claim 1, wherein the moveable member is a blade; and
   wherein the moveable member is in the first position when a distal end of the blade is moved beyond a distal end of the pair of working arms.

16. An instrument comprising:
   a pair of working arms comprising:
      i. a first arm;
      ii. a second arm;
      iii. a first electrode located on the first arm;
      iv. a second electrode located on the second arm;
      v. a passive circuit element located on the first arm or the second arm; and
      vi. a moveable member comprising a first terminal and a second terminal;
      wherein the moveable member is moveable to a first position and a second position;
      wherein in the first position, the first terminal is in electrical communication with the first electrode and the second terminal is in electrical communication with the second electrode to form a completed electrical circuit, the completed electrical circuit including the passive circuit element; and
      wherein the instrument is adapted to provide a modality based on a measured impedance of the passive circuit element in the completed electrical circuit.

17. The instrument of claim 16, wherein the moveable member comprises a second passive circuit element in electrical communication with the first terminal and the second terminal; and
   wherein the completed electrical circuit also includes the second passive circuit element.

18. The instrument of claim 16, wherein the pair of working arms comprise:
   vii. a third electrode located on the first arm; and
   viii. a fourth electrode located on the second arm;
   wherein the first arm or the second arm comprises a second passive circuit element;
   wherein the moveable member is moveable to a third position;
   wherein in the third position the first terminal is in electrical communication with the third electrode and the second terminal is in electrical communication with the fourth electrode to form a completed second electrical circuit, the completed second electrical circuit including the second passive circuit element;
   wherein the instrument is adapted to provide a second modality based on a measured impedance of the second passive circuit element in the completed second electrical circuit.

19. An instrument comprising:
   a pair of working arms comprising:
      i. a first arm;
      ii. a second arm;
      iii. a first electrode located on the first arm; and
      iv. a second electrode located on the second arm; and
   a moveable member comprising:
      i. a passive circuit element;
      ii. a first terminal; and iii. a second terminal;
wherein the moveable member is moveable to a first position and to a second position;
wherein in the first position, the first terminal is in electrical communication with the first electrode and the second terminal is in electrical communication with the second electrode to form a completed electrical circuit;
wherein the instrument is adapted to provide a modality based on an impedance of the completed electrical circuit; and
wherein in the second position, at least one of the first terminal and the second terminal is free of electrical communication with the respective first electrode and second electrode so that the electrical circuit is open.

20. An instrument comprising:
a pair of working arms comprising:
  i. a first arm;
  ii. a second arm;
  iii. a first electrode located on the first arm; and
  iv. a second electrode located on the second arm; and
a moveable member comprising:
  i. a passive circuit element;
  ii. a first terminal; and
  iii. a second terminal;
wherein the moveable member is moveable to a first position and to a second position;
wherein in the first position, the first terminal is in electrical communication with the first electrode and the second terminal is in electrical communication with the second electrode to form a completed electrical circuit;
wherein in the second position, at least one of the first terminal and the second terminal is free of electrical communication with the respective first electrode and second electrode so that the electrical circuit is open;
wherein the completed electrical circuit comprises the passive circuit element; and
wherein a controller is configured to measure an impedance of the passive circuit element in the completed electrical circuit and convert the measured impedance into an encoder signal to determine that the moveable member is in the first position or in the second position.

* * * * *